United States Patent [19]

Engelstoft et al.

[11] Patent Number: 4,645,773
[45] Date of Patent: Feb. 24, 1987

[54] β-CARBOLINE-3-OXADIAZOLYL DERIVATIVES, AND THEIR USE AS PSYCHOTROPIC AGENTS

[75] Inventors: Mogens Engelstoft, Vaerlose; Tage Honoré, Maaloev; Frank Wätjen, Bajsvaerd; Erling N. Petersen, Glostrup, all of Denmark; Andreas Huth, Berlin, Fed. Rep. of Germany

[73] Assignee: Schering Aktiengesellschaft, Berlin and Bergkamen, Fed. Rep. of Germany

[21] Appl. No.: 734,219

[22] Filed: May 15, 1985

[30] Foreign Application Priority Data

May 15, 1984 [DK] Denmark .................. 2400/84

[51] Int. Cl.$^4$ .................. A61K 31/395; C07D 471/04
[52] U.S. Cl. .................. 514/292; 546/85; 546/86; 546/87
[58] Field of Search .................. 546/85, 86, 87; 514/292

[56] References Cited

U.S. PATENT DOCUMENTS 4,435,403  3/1984  Braestrup et al. .................. 546/86

OTHER PUBLICATIONS

Marjorie et al, Metameconine as a Model Compound in the Study of Aromatic Reactions, Aug. 1962, pp. 2402–2408.

Primary Examiner—Henry R. Jiles
Assistant Examiner—J. Richter
Attorney, Agent, or Firm—Millen & White

[57] ABSTRACT

New β-carboline-3-oxadiazolyl derivatives have the general formula I:

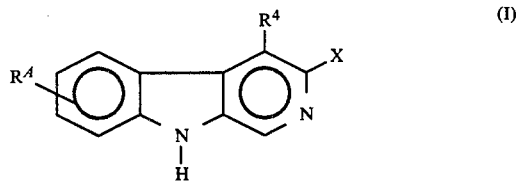

wherein X is

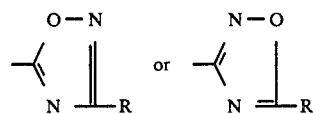

and wherein $R^4$, $R^A$ and R have specified meanings.

These new compounds exhibit surprising psychotropic properties.

18 Claims, No Drawings

β-CARBOLINE-3-OXADIAZOLYL DERIVATIVES, AND THEIR USE AS PSYCHOTROPIC AGENTS

BACKGROUND OF THE INVENTION

This invention relates to new β-carboline-3-oxadiazolyl derivatives. These new compounds possess valuable pharmacological properties which make them useful in psychopharmaceutical preparations.

EP patent publications Nos. 30254 and 54507 disclose various substituted β-carbolines including 3-oxadiazolyl derivatives which are related to the compounds of the invention. See also U.S. Pat. No. 4,371,536 and U.S. Pat. No. 4,435,403.

SUMMARY OF THE INVENTION

It is an object of this invention to provide new compounds having valuable pharmacological properties.

Upon further study of the specification and appended claims, further objects and advantages of this invention will become apparent to those skilled in the art.

These objects have been achieved by providing new β-carboline-3-oxa-diazolyl derivatives of formula I:

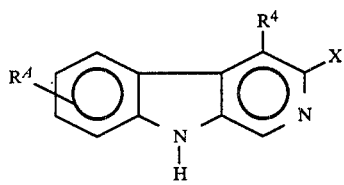

wherein

X is an oxadiazolyl group

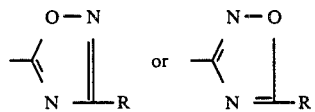

wherein

R is H, lower alkyl or cycloalkyl, $R^4$ is H, lower alkyl or lower alkoxyalkyl, $R^A$ is lower alkyl; hydroxy-lower-alkyl; $SCH_3$; $SC_2H_5$; $OR^{15}$; $CH_2OR^{17}$; $-C\equiv C-CH_2N(CH_3)_2$; or

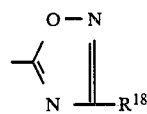

$R^{15}$ is lower alkyl, phenyl-$C_{1-3}$-alkyl, cycloalkyl or cycloalkenyl;

$R^{17}$ is H, lower alkyl or phenyl;

$R^{18}$ is lower alkyl, and wherein the compound I may contain one or two $R^A$ groups, provided, however, that X is not 3-ethyl-1,2,4-oxadiazole-5-yl when $R^4$ is H and $R^A$ is 5—$CH_2OCH_3$, 5—$OCH_2C_6H_5$, 6—$SCH_3$, 6$OCH_3$ or 6—$OCH_2C_6H_5$.

DETAILED DISCUSSION

The term "lower" refers to 1–6 carbon atoms. The term "lower alkyl" and corresponding alkyl portions of other groups include alkyl groups containing from 1 to 6 carbon atoms, e.g., methyl, ethyl, n-propyl, isopropyl, n-butyl, isobutyl, sec-butyl, tert-butyl, a pentyl, a hexyl, etc. Cycloalkyl is of 3–7 C atoms, e.g. cyclopropyl, cyclobutyl, cyclopentyl, cyclohexyl, cycloheptyl, etc. Corresponding cycloalkyl groups are included in "cycloalkenyl".

Surprisingly, it has been found that the compounds of the invention exhibit psychotropic properties which are clearly superior to those of the prior art compounds.

The superior psychotropic properties of the compounds of the invention are evidenced by their improved capability for displacing radioactively labelled flunitrazepam from benzodiazepine receptors. It is well known (Squires, R. F. and Braestrup, C., Nature (London) 266 (1977)) that specific sites in the central nervous systems of vertebrates exhibit a high specific affinity for binding 1,4- and 1,5-benzodiazepines. These sites are called benzodiazepine receptors. The displacement activity of the compounds of the invention has been determined by determining the $IC_{50}$ value and the $ED_{50}$ value.

The $IC_{50}$ value represents the concentration which causes a displacement of 50% of the specific binding of $^3H$-flunitrazepam (1.0 nM, 0° C.) in samples comprising a total volume of 0.55 ml of a suspension of brain membrane, e.g from rats.

The displacement test is performed as follows:

0.50 ml of a suspension of non-treated rat forebrain in 25 mM $KH_2PO_4$, pH=7.1 (5–10 mg tissue/sample) is incubated for 40–60 minutes at 0° C. together with $^3H$-diazepam (specific activity 87 Ci/mmol, 1.0 nM) or $^3H$-flunitrazepam (specific activity 87 Ci/mmol, 1.0 nM). After incubation, the suspension is filtered through "Whatman GF/C" glass fiber filters, the residue washed twice with cold buffer solution and the radioactivity measured by scintillation counting.

The test is repeated except that prior to the addition of the radioactive labelled benzodiazepine, a given amount or an excessive amount of the compound, the displacement capability of which is to be determined, is added. Based on the data obtained the $IC_{50}$ value can be calculated.

The $ED_{50}$ value represents the dose (mg/kg) of a test substance which causes the specific binding of flunitrazepam to benzodiazepine receptors in a living brain to be reduced to 50% of the control value. Such an in vivo test is carried out as follows:

Groups of mice are injected with the test substance at different doses and usually subcutaneously. 15 minutes later $^3H$-flunitrazepam is administered intravenously to the mice and after further 20 minutes the mice are killed. Their forebrain membranes are removed and the radioactivity of these forebrain membranes is measured by scintillation counting. The $ED_{50}$ value is determined from dose-response curves.

Test results obtained by testing some compounds of the invention will appear from the following Table 1.

TABLE 1

Affinity for the benzodiazepine receptor inhibition of $^3$H—flunitrazepam binding

| X | $R^4$ | $R^A$ | IC$_{50}$ ng/ml (in vitro) | ED$_{50}$ mg/kg (in vivo) |
|---|---|---|---|---|
| O—N, N, Me (oxadiazole-Me) | CH$_2$OCH$_3$ | 5-OCH$_2$Ph | 0.4 | 0.9 |
| N—O, N, Et | CH$_2$OCH$_3$ | 5-OCH$_2$Ph | 0.5 | 1.0 |
| O—N, N, Et | CH$_3$ | 5-CH$_2$OC$_2$H$_5$ | 0.26 | 0.4 |
| O—N, N, Et | CH$_3$ | 5-O—iPr | 0.5 | 0.4 |
| O—N, N, Et | CH$_2$OCH$_3$ | 5-O—iPr | 0.2 | 0.2 |
| O—N, N, Et | CH$_2$OCH$_3$ | 5-OCH$_2$CH$_2$CH$_3$ | 0.3 | 1.4 |
| O—N, N, Et | CH$_2$OCH$_3$ | 5-O-cyclohexyl | 0.4 | 0.75 |
| O—N, N, Et | H | 6-C≡C—CH$_2$NMe$_2$ | 0.4 | 7.9 |
| O—N, N, Et | CH$_2$OCH$_3$ | 5-O-cyclobutyl | 0.4 | 0.6 |

The invention also relates to a method of preparing the above mentioned compounds. This method comprises
(a) reacting a reactive derivative of a compound of the general formula II

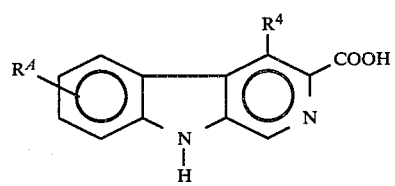

(II)

wherein $R^4$ and $R^A$ have the meanings set forth above with a compound having the formula III

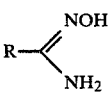

(III)

wherein R has the meaning set forth above, to form a compound of the general formula I in which X is

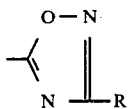

wherein R has the meaning set forth above, (b) reacting a compound having the general formula IV

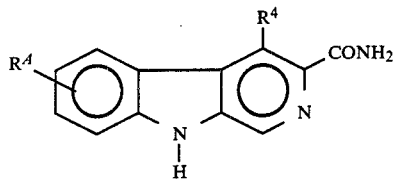

wherein $R^4$ and $R^A$ have the meanings set forth above, with a compound V having the general formula

R—C(OCH₃)₂N(CH₃)₂      (V)

wherein R has the meaning set forth above, to form a compound having the general formula VI

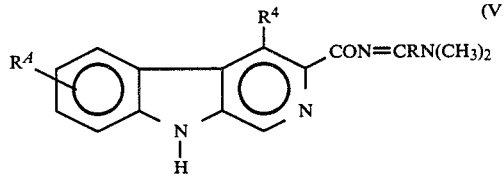

wherein R, $R^4$ and $R^A$ have the meanings set forth above and by reacting the compound having the formula VI with NH₂OH or another aminating agent, to form a compound having the formula I, wherein X is

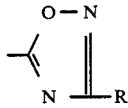

wherein R has the meaning set forth above or (c) reacting a compound having the formula VII

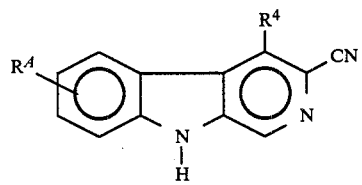

wherein $R^4$ and $R^A$ have the meanings set forth above with NH₂OH, to form a compound having the general formula VIII

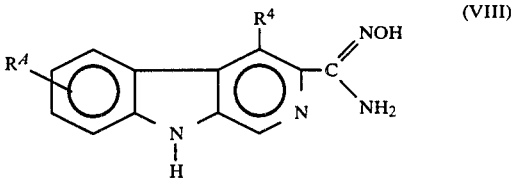

wherein $R^4$ and $R^A$ have the meanings set forth above, and by reacting the compound having the formula VIII with a compound having the general formula IX (RCO)₂O      (IX)

wherein R has the meaning set forth above, to form a compound having the formula I, wherein X is

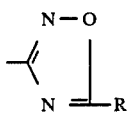

wherein R has the meaning set forth above.

All of the starting materials required in these processes are known or readily preparable from known starting materials using conventional processes; see, e.g., U.S. Pat. No. 4,435,403.

The processes of this invention are per se known and can be conducted under fully conventional conditions and considerations. See, e.g., U.S. Pat. No. 4,371,536 and U.S. Pat. No. 4,435,403.

The pharmacologically active compounds of the invention can be used for the formulation of pharmaceutical preparations, e.g. for oral and parenteral administration to mammals including humans, in accordance with conventional methods of galenic pharmacy. Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salts for influencing osmotic pressure, buffers and/or coloring substances and the like, which do not deleteriously react with the active compounds.

Injectable solutions or suspensions, preferably aqueous solutions with the active compound dissolved in polyhydroxyethoxylated ricinus oil, are particularly suitable for parenteral use.

Ampoules are convenient unit dosages.

Tablets, dragees or capsules having talc and/or a carbohydrate carrier or binder or the like, the carrier preferably being lactose and/or corn starch and/or potato starch, are particularly suitable for oral application. A syrup, elixir or the like can be used wherein a sweetened vehicle can be employed.

Generally, the compounds of this invention are dispensed in unit dosage form comprising 0.05–100 mg in a pharmaceutically acceptable carrier per unit dosage.

The dosage of the compounds according to this invention is 0.1–300 mg/day, preferably 0.5–30 mg/day, when administered to patients, e.g. humans, as a drug.

All compounds of this invention have affinity for benzodiazepine receptors. Consequently, they have a spectrum of the activities of the benzodiazepines, e.g., muscle relaxant, sedative, anxiolytic or anticonvulsant and are useful for the conventional corresponding indications, e.g., as muscle relaxants, antiepileptics, sedatives, hypnotics, tranquilizers, etc. These activities can be agonistic to antagonistic to inverse agonistic, the corresponding indications being conventional in each case, e.g., antagonistically they can be used to reverse benzodiazepine effects, e.g., in cases of overdose, inverse agonistically they can be used to achieve the inverse effects of the benzodiazepines, e.g., they can be used as vigilance enhancers, etc. The type and level of activity for a given dosage of each compound can be conventionally determined by routine experimentation using well known pharmacological protocols for each of the activities; the corresponding indications treatable at that dosage will be well known to skilled workers based on the pharmacological results. The compounds of this invention are particularly noteworthy for their anxiolytic, anticonvulsant, muscle relaxant and hypnotic activity, e.g., to treat anxiety, epilepsy, muscle spasms and insomnia at the above dosages analogously to the known agent diazepam.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

3-[5-(3-ethyl-1,2,4-oxadiazole)-yl]-4-methoxymethyl-5-benzyloxy-β-carboline

A: Pripionamide oxime

A solution of 2.3 g of sodium in 40 ml of methanol was added dropwise to a solution of 6.9 g of hydroxylamine hydrochloride in 100 ml of methanol. The reaction mixture was left for one hour before it was filtered. 0.11 mole propionnitrile was added dropwise to the filtrate, and the reaction mixture was allowed to stand for 2 days at room temperature with exclusion of water.

B: 3-[5-(3-ethyl-1,2,4-oxadiazole)-yl]-4-methoxymethyl-5-benzyloxy-β-carboline

To 27.2 g of imidazol in 300 ml of dry tetrahydrofuran (THF) was added dropwise 7.2 ml of thionylchloride in 100 ml of dry THF at room temperature while stirring. After the addition, stirring was continued for 0.5 hours, and the precipitate was removed by filtration. The filtrate contained 0.1 mole of thionyldiimidazole per 400 ml.

10 g of 4-methoxymethyl-5-benzyloxy-β-carboline-3-carboxylic acid were suspended in 300 ml of dry THF. 200 ml of thionyldiimidazole in THF were added dropwise while stirring and stirring was continued until all acid had reacted.

10 g of propionamide oxime were added dropwise during 5 minutes and stirring was continued for some hours. The mixture was left at room temperature until next day. The mixture was then evaporated and 200 ml of water and acetic acid were added. The mixture was filtered yielding 11.7 g of product. This product was dissolved in 900 ml of xylene and heated to 155°–165° C. while stirring for 6 hours. The xylene phase was filtered giving 11.5 g of crude product. The crude product was purified by chromatography on silica gel and CHCl₃—Et₃N—CH₃O (1:1:1) yielding 9.0 g of pure 4-methoxymethyl-5-benzyloxy-3-[5-(3-ethyl-1,2,4-oxadiazole)-yl]-β-carboline. M.p. 182°–7° C.

The following compounds were prepared in an analogous manner:

3-[5-(3-ethyl-1,2,4-oxadiazole)-yl]-4-methoxymethyl-6-benzyloxy-β-carboline. M.p. 169°–73° C.

3-[5-(3-methyl-1,2,4-oxadiazole)-yl]-4-methoxymethyl-5-benzyloxy-β-carboline. M.p. 236°–39° C.

3-[5-(3-cyclopropyl-1,2,4-oxadiazole)-yl]-4-methoxymethyl-5-benzyloxy-β-carboline. M.p. 214°–9° C.

3-[5-(3-ethyl-1,2,4-oxadiazole)-yl]-4-methyl-5-benzyloxy-β-carboline. M.p. 224°–7° C.

3-[5-(3-ethyl-1,2,4-oxadiazole)-yl]-4-methoxymethyl-6-methylthio-β-carboline.

3-[5-(3-ethyl-1,2,4-oxadiazole)-yl]-6,7-dimethoxy-4-ethyl-β-carboline.

3,6-di-[5-(3-ethyl-1,2,4-oxadiazole)-yl]-4-methyl-β-carboline.

3-[5-(3-ethyl-1,2,4-oxadiazole)-yl]-4-methyl-5-ethoxymethyl. M.p. 192°–4° C.

3-[5-(3-ethyl-1,2,4-oxadiazole)-yl]-4-ethyl-5-methoxy-β-carboline. M.p. 120°–4° C.

3-[5-(3-ethyl-1,2,4-oxadiazole)-yl]-4-ethyl-6-methoxy-β-carboline. M.p. 186°–215° C.

3-[5-(3-ethyl-1,2,4-oxadiazole)-yl]-4-ethyl-6-(3-dimethylaminopropargyl)-β-carboline. M.p. 148°–56° C.

3-[5-(3-ethyl-1,2,4-oxadiazole)-yl]-4-methyl-6-methylthio-β-carboline. M.p. 260°–5° C.

3-[5-(3-ethyl-1,2,4-oxadiazole)-yl]-6-(3-dimethylaminopropargyl)-β-carboline. M.p. 225°–30° C.

3-[5-(3-ethyl-1,2,4-oxadiazole)-yl]-6-ethylthio-β-carboline. M.p. 188°–93° C.

2-[5-(3-ethyl-1,2,4-oxadiazole)-yl]-4-methyl-5-isopropoxy-β-carboline. M.p. 232°–5° C.

3-[5-(3-ethyl-1,2,4-oxadiazole)-yl]-5-iso-propoxy-β-carboline. M.p. 267°–71° C.

3-[5-(3-ethyl-1,2,4-oxadiazole)-yl]-5-ethoxymethyl-β-carboline. M.p. 105°–12° C.

3-[5-(3-ethyl-1,2,4-oxadiazole)-yl]-4-methoxymethyl-5-ethoxymethyl-β-carboline. M.p. 105°–12° C.

3-[5-(3-ethyl-1,2,4-oxadiazole)-yl]-4-methoxymethyl-5-ethoxy-β-carboline. M.p. 74°–88° C.

3-[5-(3-ethyl-1,2,4-oxadiazole)-yl]-6-ethoxy-β-carboline. M.p. 243°–53° C.

3-[5-(3-ethyl-1,2,4-oxadiazole)-yl]-6-(hydroxybutyl)-β-carboline. M.p. 176°–9° C.

3-[5-(3-ethyl-1,2,4-oxadiazole)-yl]-4-methoxymethyl-6-isopropyl-β-carboline. M.p. 174° C.

3-[5-(3-ethyl-1,2,4-oxadiazole)-yl]-4-methoxymethyl-5-(cyclohexen-3-yl)oxy-β-carboline.

3-[5-(3-ethyl-1,2,4-oxadiazole)-yl]-4-methoxymethyl-5-isobutoxy-β-carboline. M.p. 93.8° C.

3-[5-(3-ethyl-1,2,4-oxadiazole)-yl]-4-methoxymethyl-6-ethoxymethyl-β-carboline. M.p. 168°–71° C.

3-[5-(3-ethyl-1,2,4-oxadiazole)-yl]-4-methoxymethyl-5-isopropoxy-β-carboline. M.p. 138°–42° C.

3-[5-(3-ethyl-1,2,4-oxadiazole)-yl]-4-methoxymethyl-5-propoxy-β-carboline. M.p. 104°-22° C.
3-[5-(3-ethyl-1,2,4-oxadiazole)-yl]-4-methyl-5-methoxymethyl-β-carboline. M.p. 205°-10° C.
3-[5-(3-ethyl-1,2,4-oxadiazole)-yl]-4-methyl-5-methyl-β-carboline. M.p. 242°-4° C.
3-[5-(3-ethyl-1,2,4-oxadiazole)-yl]-4-ethyl-5-ethoxymethyl-β-carboline. M.p. 156°-63° C.
3-[5-(3-ethyl-1,2,4-oxadiazole)-yl]-4-methyl-5-ethoxyethyl-β-carboline. M.p. 180°-4° C.
3,5-di-[5-(3-ethyl-1,2,4-oxadiazole)-yl]-β-carboline. M.p. 226°-30° C.
3-[5-(3-ethyl-1,2,4-oxadiazole)-yl]-4-methoxymethyl-5-cyclo-butoxy-β-carboline. M.p. 107°-11° C.
and
3-[5-(3-ethyl-1,2,4-oxadiazole)-yl]-4-methoxymethyl-6-iso-propyloxy-β-carboline. M.p. 176°-9° C.

EXAMPLE 2

4-methoxymethyl-5-benzyloxy-3-[-(5-ethyl-1,2,4-oxadiazole)-yl]-β-carboline

A: 4-methoxymethyl-5-benzyloxy-β-carboline-3-carboxamide oxime

A mixture of 0.0125 mol and 3-cyano-4-methoxymethyl-5-benzoloxy-β-carboline, 1.1 g of hydroxylamine hydrochloride, 200 ml of 99% ethanol and 5.2 ml of a 20% potassium carbonate solution in water was refluxed for 22 hours. The reaction mixture was filtered and the filtrate was concentrated. The residue was treated with 100 ml of water and the crystalline solid was filtered off and washed with water.

B: 4-methoxymethyl-5-benzyloxy-3-[-3-(5-ethyl-1,2,4-oxadiazole)-yl]-β-carboline

A mixture of 5.6 mmol of the product of A and 10 ml of propionic acid anhydride was stirred for 2 hours at .20° C. and thereafter for 5 hours at 120° C. After evaporation 100 ml of THF were added and the mixture was allowed to stand overnight at room temperature whereafter the mixture was concentrated in vacuo. 100 ml of methylene chloride were added and the mixture was filtered leaving the title compound. M.p. 173.7° C.

The following compounds were prepared in an analogous manner:
3-[3-(5-methyl-1,2,4-oxadiazole)-yl]-4-methoxymethyl-5-benzyloxy-β-carboline. M.p. 168.5° C.
3-[-3-(5-ethyl-1,2,4-oxadiazole)-yl]-4-methyl-5-ethoxymethyl-β-carboline. M.p. 152°-65° C.

What is claimed is:
1. A β-carboline-3-oxadiazolyl of the formula

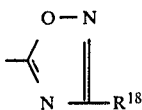

wherein
X is an oxadiazolyl group of the formula

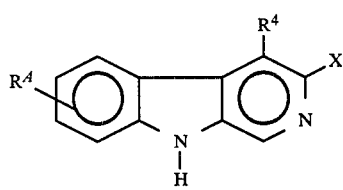

wherein R is H, C$_{1-6}$-alkyl or C$_{3-7}$-cycloalkyl,
R$^4$ is H, C$_{1-6}$-alkyl or C$_{1-6}$-alkoxyalkyl, R$^A$ is C$_{1-6}$-alkyl, hydroxy-C$_{1-6}$-alkyl; SCH$_3$; SC$_2$H$_5$; OR$^{15}$; CH$_2$OR$^{17}$; C≡C—CH$_2$N(CH$_3$)$_2$; or

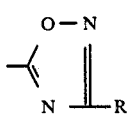

R$^{15}$ is C$_{1-6}$-alkyl, phenyl-C$_{1-3}$-alkyl, C$_{3-7}$-cycloalkyl or C$_{3-7}$-cycloalkenyl;
R$^{17}$ is H, C$_{1-6}$-alkyl or phenyl;
R$^{18}$ is C$_{1-6}$-alkyl, and
n is 1 or 2,
provided that X is not 3-ethyl-1,2,4-oxadiazole-5-yl when R$_4$ is H and R$^A$ is 5—CH$_2$OCH$_3$, 5—OCH$_2$C$_6$H$_5$, 6—SCH$_3$, 6—OCH$_3$ or 6—OCH$_2$C$_6$H$_5$.

2. A compound of claim 1 wherein X is

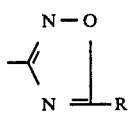

3. A compound of claim 1 wherein X is

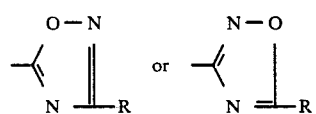

4. A compound of claim 1 wherein R is methyl or ethyl.
5. A compound of claim 1 wherein R$^4$ is methyl, ethyl or methoxymethyl.
6. A compound of claim 1 wherein R$^A$ is benzyloxy.
7. A compound of claim 1 wherein R$^A$ is isopropoxy, ethoxymethyl, propoxy, cyclohexenyloxy, 3-dimethylamino propargyl or cyclobutoxy.
8. 4-Methoxymethyl-5-benxyloxy-3-[5-(3-ethyl-1,2,4-oxadiazole)-yl]-β-carboline, a compound of claim 1.
9. 4-Methoxymethyl-5-benzyloxy-3-[5-(3-methyl-1,2,4-oxadiazole)-yl]-β-carboline, a compound of claim 1.
10. 3-[5-(3-Ethyl-1,2,4-oxadiazole)-yl]-5-isopropoxy-β-carboline, a compound of claim 1.
11. 3-[5-(3-Ethyl-1,2,4-oxadiazole)-yl]-4-methyl-5-methoxymethyl-β-carboline, a compound of claim 1.
12. A pharmaceutical composition comprising a compound of claim 1 and a pharmaceutically acceptable carrier.
13. A composition of claim 9, wherein the amount of said compound is 0.05-100 mg.
14. A method of achieving a psychotropic effect comprising administering an amount of a compound of claim 1.
15. A compound of claim 1, wherein R$^A$ is OR$^{15}$.
16. A compound of claim 1, wherein R$^A$ is C$_{1-6}$-alkyl.
17. A compound of claim 1, wherein R$^A$ is C$_{1-6}$-alkyl, OR$^{15}$, CH$_2$OR$^{17}$ or C≡C—CH$_2$N(CH$_3$)$_2$.
18. A compound of claim 1, wherein R$^A$ is

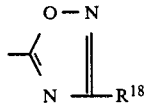

* * * * *